(12) United States Patent
Li

(10) Patent No.: US 9,055,976 B2
(45) Date of Patent: Jun. 16, 2015

(54) MULTI-DIRECTIONAL DISTRACTOR

(75) Inventor: Jiangming Li, Shijiazhuang (CN)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 857 days.

(21) Appl. No.: 13/319,148

(22) PCT Filed: Nov. 11, 2010

(86) PCT No.: PCT/CN2010/078632
§ 371 (c)(1),
(2), (4) Date: Nov. 7, 2011

(87) PCT Pub. No.: WO2012/061987
PCT Pub. Date: May 18, 2012

(65) Prior Publication Data
US 2012/0239035 A1 Sep. 20, 2012

(51) Int. Cl.
*A61B 17/66* (2006.01)
(52) U.S. Cl.
CPC .................................. *A61B 17/663* (2013.01)
(58) Field of Classification Search
CPC ..................................................... A61B 17/663
USPC ....................................... 606/55, 57, 71, 282
See application file for complete search history.

(56) References Cited

U.S. PATENT DOCUMENTS

| | | |
|---|---|---|
| 7,195,481 B1 | 3/2007 | Linck |
| 2005/0256526 A1 | 11/2005 | Johnston |
| 2006/0015118 A1* | 1/2006 | Richter et al. .................. 606/90 |
| 2006/0079902 A1* | 4/2006 | Johnston ......................... 606/71 |
| 2007/0038217 A1* | 2/2007 | Brown et al. ................... 606/57 |
| 2007/0043370 A1 | 2/2007 | Ueda et al. |
| 2007/0162045 A1* | 7/2007 | Ahmad .......................... 606/105 |
| 2008/0039861 A1* | 2/2008 | Ahmad et al. ................ 606/105 |

FOREIGN PATENT DOCUMENTS

| | | |
|---|---|---|
| CN | 101040793 A | 9/2007 |
| CN | 200960192 Y | 10/2007 |
| WO | 1999004713 | 2/1999 |

OTHER PUBLICATIONS

International Search Report and Written Opinion mailed Aug. 18, 2011 as received in international application No. PCT/CN2010/078632.

\* cited by examiner

*Primary Examiner* — Jerry Cumberledge
*Assistant Examiner* — Nicholas Plionis
(74) *Attorney, Agent, or Firm* — Maschoff Brennan

(57) ABSTRACT

A mandibular distractor can include an elongated main body having a central longitudinal axis extending in the elongate direction between a first end and a spaced apart second end. A first bone mount can be secured to the main body and a second bone mount can be positioned on the main body. A drive mechanism configured to selectively move the second bone mount longitudinally along the main body can also be included. A third bone mount configured to be moved longitudinally along the main body can also be included.

19 Claims, 12 Drawing Sheets

MULTI-DIRECTIONAL DISTRACTOR

CROSS-REFERENCE TO RELATED APPLICATIONS

The present application is a U.S. National Stage application filing under 35 USC §371 of International Application No. PCT/CN2010/078632, filed on Nov. 11, 2010.

BACKGROUND

In mandibular distraction osteogenesis, the lower jaw is surgically cut into two portions and separated by a mandibular distractor to allow the bone to grow in the gap between the two pieces. As the bone grows into the gap, the two portions are separated further by manipulating the mandibular distractor until the desired separation is achieved. Currently, in mandibular distraction osteogenesis treatment, the distractor often can only be adjusted in its longitudinal direction. However, in conventional surgery for skeletal traction, the final position in the jaw typically cannot be accomplished with fraction in only a single direction. Besides longitudinal stretching, the distracted portion of the jay may also need rotation in the angular direction with respect to the other portion of the jaw, so that the final dentition occlusion is in the correct position. To this end, there are three conventional options available to solve the problem: 1) use of an arc tractor to provide the rotational movement; 2) use of two straight tractors, with the completion of one or two surgeries; or 3) use of drifting or rotating technology. However, the arc tractor is expensive and the surgery required to position and use the arc tractor may need to be completed in phases; the drifting or rotating technology has low reliability and a small incision surgery is needed before the rotation to remove part of the fixing screws. Also, multiple surgeries is not desirable. All of these tend to increase the patient's expense and suffering.

SUMMARY

In one aspect, a mandibular distractor can include an elongated main body having a central longitudinal axis extending in the elongate direction between a first end and a spaced apart second end. A first bone mount can be secured to the main body and a second bone mount can be positioned on the main body. A drive mechanism configured to selectively move the second bone mount longitudinally along the main body can also be included. A third bone mount configured to be moved longitudinally along the main body can also be associated with the main body.

In another aspect, a mandibular distractor can include an elongated main body having a central longitudinal axis extending in the elongate direction between a first end and a spaced apart second end. A first bone mount configured to attach to a first bone portion can be secured to the main body and a second bone mount can be positioned on the main body. The second bone mount can include an engaging member and a bone plate configured to attach to a second bone portion. The bone plate can be hingedly attached to the engaging member. A drive mechanism configured to selectively move the second bone mount longitudinally along the main body can also be attached to the engaging member.

In another aspect, a method of performing distraction osteogenesis can include attaching a first bone mount to a first bone portion, the first bone mount being secured to an elongated main body of a mandibular distractor, the main body having a central longitudinal axis extending in the elongate direction between a first end and a spaced apart second end; attaching a second bone mount to a second bone portion, the second bone mount being positioned on the main body; attaching a third bone mount to the second bone portion, the third bone mount being associated with the main body; and activating a drive mechanism to selectively move the second bone mount longitudinally along the main body away from the first bone mount, thereby causing the second bone portion to separate from the first bone portion.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
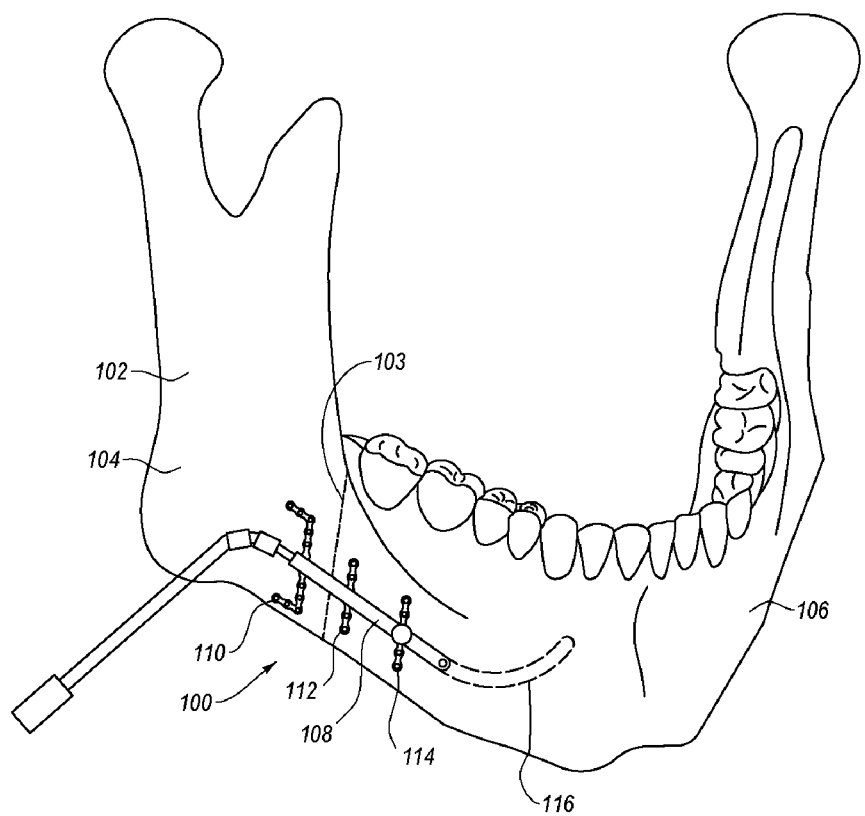
FIG. 1 is a perspective view of an illustrative embodiment of a mandibular distractor attached to a jaw.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Furthermore, as used in the specification and appended claims, directional terms, such as "top," "bottom," "up," "down," "upper," "lower," "proximal," "distal," and the like are used herein solely to indicate relative directions in viewing the drawings and are not intended to limit the scope of the claims in any way.

Generally, a distractor can be used during distraction osteogenesis to slowly separate first and second portions of a lower jaw or other bone and provide a gap between the bone portions for bone growth to occur. This allows the mandibular deformity of micromandile or asymmetry to be reshaped by the neogenesis bony matrix in the gap that then becomes calcificated. The distractor can be used for any desired gap width generally used in the art of bone distraction. For example, during a typical distraction osteogenesis, the gap can be widened by between 0 mm and 2 mm a day until a total gap width of up to 70 mm is obtained. Other daily and total gap widths are also possible. Furthermore, the distractor can be used for distraction of any bone. For example, the distractor can be used to provide gaps in a mandible, a femur, a long bone, or any other bone.

As discussed in more detail below, the distractor can include an elongated main body having a central longitudinal axis extending in the elongate direction between a first end and a spaced apart second end. The longitudinal axis can be substantially linear. A first bone mount can be rigidly secured to the main body and a second bone mount can be moveably positioned on the main body. A drive mechanism can be included that selectively moves the second bone mount longitudinally along the main body. The positioning and movement of the second bone mount are generally selective because they are directly dependent on the movement of the drive mechanism. As discussed in detail below, the first bone mount can be configured to attach to the first bone portion and the second bone mount can be configured to attach to the second bone portion. Also as discussed below, a third bone mount configured to be moved longitudinally along the main body can also be associated with the main body. The third bone mount can also be configured to attach to the second bone portion.

As discussed below, the main body can have an inner surface bounding a bore extending longitudinally between the first and second ends. A channel can be formed on the main body that communicates with the bore.

The drive mechanism can include a screw drive or other type of drive mechanism positioned within the main body or a hydraulic equipment system, as is known to one of skill in the art. For example, as described in detail below, the drive mechanism can include a screw drive positioned within the bore of the main body. The screw drive can be positioned within the bore of the main body so as to align with the central longitudinal axis. The mandibular distractor can also include a drive actuator that engages and activates the drive mechanism. As discussed below, the drive actuator can include a coupler, a universal joint, and/or a handle and may be disengageable from the drive mechanism. For example, when a screw drive is used, the coupler can releasably engage and rotate the screw drive, as discussed below.

The first bone mount can be positioned at the first end of the main body and can include a first bone plate coupled to the main body. For example, the first bone plate can be rigidly secured to or integrally formed with the main body, as discussed below. The first bone plate can have a bone contact surface and can be configured to attach to the first bone portion as discussed below.

The second bone mount can engage the drive mechanism so as to be moved longitudinally with respect to the main body by the drive mechanism, as discussed in detail below. For example, when a screw drive is used as a part of the drive mechanism, the second bone mount can engage the screw drive through the channel such that rotation of the screw drive causes the second bone mount to move longitudinally along the main body. As discussed in detail below, the second bone mount can include an engaging member that engages the drive mechanism and a second bone plate attached to the engaging member. The engaging member can extend through the channel. The second bone plate can have a bone contact surface and can be hingedly attached to the engaging member as discussed below. The second bone plate can be rotatable with respect to the main body about a rotational axis as discussed below. The rotational axis can be substantially perpendicular to the central longitudinal axis of the main body. The second bone plate can be rotatable with respect to the main body about an axis that is from about 45 degrees to about substantially perpendicular to the bone contact surface. The second bone plate can be configured to attach to the second bone portion.

As discussed below, the third bone mount can be slidably disposed on the main body. The third bone mount can include a sliding ring discussed in detail below that is movable along the main body. The sliding ring can have substantially any cross sectional profile commensurate with the cross sectional profile of the main body, such as being substantially spherical. The third bone mount can also include a third bone plate attached to the sliding ring. The third bone plate can have a bone contact surface and can be hingedly attached to the sliding ring. The third bone plate can be rotatable with respect to the main body about a rotational axis. The rotational axis can be substantially perpendicular to the central longitudinal axis of the main body. The third bone plate can be rotatable with respect to the main body about an axis that is from about 45 degrees to about substantially perpendicular to the bone contact surface. The third bone plate can be configured to attach to the second bone portion.

The second bone mount can be positioned between the first bone mount and the third bone mount. The bone contact surfaces of the first, second, and third bone plates can all lie within the same plane or within one or more different planes.

The mandibular distractor can also include a curved guide rail extending from the main body. The guide rail can be substantially arcuate and have a similar cross sectional shape as the main body. The third bone mount can be freely slidable along the curved guide rail.

FIG. 1 depicts an illustrative embodiment of a mandibular distractor 100 attached to a lower jaw 102 that has been separated along a separation line 103 into first and second bone portions 104 and 106. Distractor 100 includes a main body 108 and first, second, and third bone mounts 110, 112, and 114 attached to or otherwise associated with main body 108. First bone mount 110 is attached to first bone portion 104, while second and third bone mounts 112 and 114 are both attached to second bone portion 106, as discussed in more detail below. A curved guide rail 116 can be attached to main body 108 if desired and is depicted by dashed lines in FIG. 1.

Figure 2A:
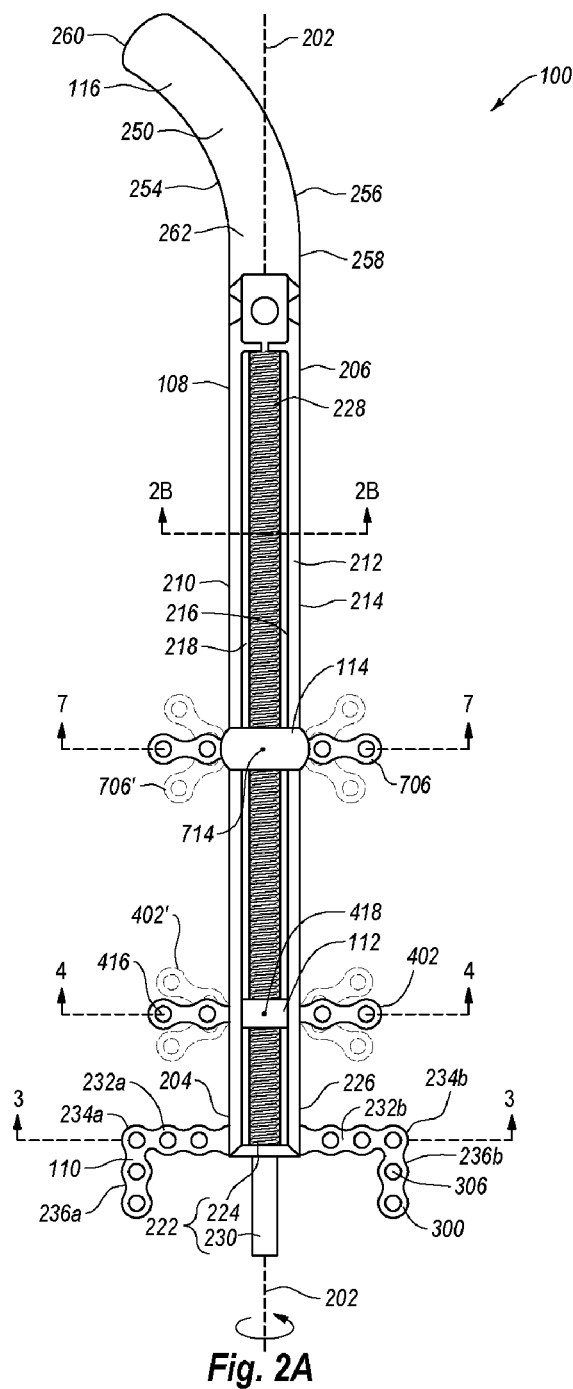
FIG. 2A is a top view of an illustrative embodiment of a mandibular distractor with a top wall of the main body removed to show details within the main body.
Figure 2B:
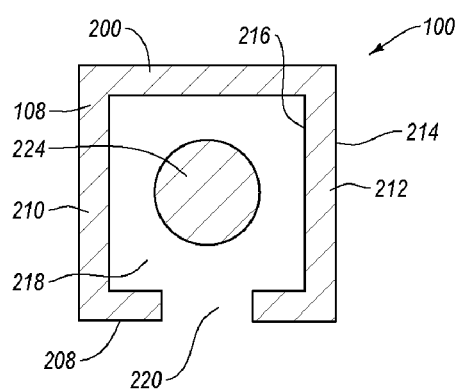
FIG. 2B is a cross sectional view of the mandibular distractor depicted in FIG. 2A taken along the section line 2B-2B.

FIG. 2A is a top view of an illustrative embodiment of distractor 100 and FIG. 2B is a cross sectional view of distractor 100 taken along the section line 2B-2B of FIG. 2A. FIG. 2B includes a top wall 200 of main body 108, which is removed from FIG. 2A to show details within the distractor. As shown in FIGS. 2A and 2B, main body 108 can have a central longitudinal axis 202 extending in an elongate direction between a first end 204 and a spaced apart second end 206. Main body 108 may be substantially linear, i.e., straight between first and second ends 204 and 206, or may be curved, if desired. Besides top wall 200, main body 108 can also include a bottom wall 208 and opposing side walls 210 and 212 extending longitudinally between first and second ends 204 and 206.

Walls 200, 208, 210, and 212 can collectively have an outer surface 214 facing away from main body 108 and an opposing inner surface 216 bounding a bore 218 extending along central longitudinal axis 202 between first and second ends 204 and 206. Bore 218 can have a substantially circular cross section or can be substantially rectangular. Bore 218 can have a diameter or cross sectional width of between about 0 mm to about 30 mm with between about 2 mm to about 5 mm being common. Other diameters or widths can also be used.

The cross sectional outer shape of main body 108 is substantially square in the depicted embodiment, with the outer surface of each wall forming a different side of the square, as shown in FIG. 2B, although other cross sectional shapes are also possible. For example, main body 108 can instead have an outer cross sectional shape that is substantially circular, oval, rectangular, or any other desired shape. Furthermore, although four separate walls 200, 208, 210, and 212 are shown, more or less walls can instead be used. For example, when main body 108 has a substantially circular or oval cross sectional shape, only a single curved wall can be used be instead of four walls, if desired. Main body 108 can be any length and width necessary to perform the bone distraction. By way of example only, main body 108 can have a length of between about 0 mm to about 100 mm with between about 30 mm to about 50 mm being common. Similarly, main body 108 can have a width of between about 0 mm to about 10 mm with between about 4 mm to about 6 mm being common. Other lengths and widths are also possible.

An elongated channel 220 can be formed on bottom wall 208 of main body 108 between inner and outer surfaces 216 and 214 to communicate with bore 218. That is, channel 220 passes completely through bottom wall 208 and extends longitudinally along all or part of the length of bore 218. As depicted in FIG. 2B, channel 220 generally has a width less than bore 218, although the width of channel 220 may be the same as that of bore 218, if desired. As discussed below, second bone mount 112 can extend through channel 220 so as to attach to the bone. As shown in the depicted embodiment, main body 108 is substantially linear along its entire length, although this is not required.

As shown in FIG. 2A, a drive mechanism 222 can be positioned within bore 218 of main body 108. Drive mechanism 222 is used to selectively move second bone mount 112 longitudinally along main body 108. Drive mechanism 222 can include a threaded screw drive 224 extending longitudinally between a first end 226 and a spaced apart second end 228. Screw drive 224 can be positioned within bore 218 of main body 108 so as to align with central longitudinal axis 202. Second end 228 of screw drive 224 can be rotatably attached to second end 206 of main body 108 within bore 218 while first end 226 is positioned at first end 204 of main body 108.

Drive mechanism 222 can also include a first coupler 230 extending longitudinally away from first end 226 of screw drive 224. First coupler 230 can be configured to releasably engage with a drive actuator, as discussed below. First coupler 230 can be in the form of a recessed socket, a key, a latching mechanism or other coupling element known by one skilled in the art. Furthermore, any kind of corresponding universal joint pair can be used or a bar of soft material which can be bent easily but is strong enough to be rotated along its curved longitudinal axis. For example a silicone tube having its wall strengthened (e.g. with wires winding along the long axis) but having rigidly fixed ends can also be used. In addition, first coupler can be accomplished by splicing, welding a helical conjunction which has been designed by precise calculation of its final direction, etc, as is known by one skilled in the art.

It is appreciated that screw drive 224 is but one example of a drive mechanism that can be used and that other types of drive mechanisms can alternatively be used. For example, drive mechanism can alternatively include a hydraulic drive system or the like.

Figure 3:
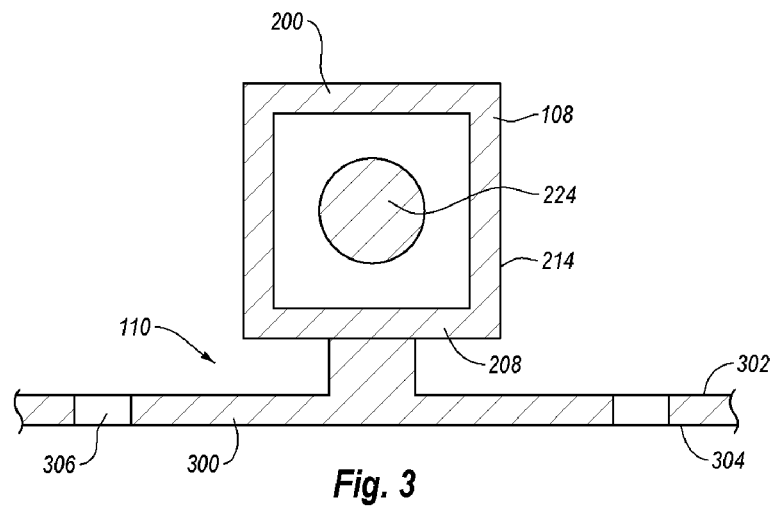
FIG. 3 is a cross sectional view of the mandibular distractor depicted in FIG. 2A taken along the section line 3-3 to show details of a first bone mount.

FIG. 3 is a cross sectional view of distractor 100 taken along the section line 3-3 of FIG. 2A to show details of first bone mount 110. Similar to FIG. 2B, FIG. 3 depicts top wall 200 of main body 108, which is removed from FIG. 2A. Turning to FIG. 3 in conjunction with FIG. 2A, first bone mount 110 can include a substantially flat first bone plate 300 mounted to bottom wall 208 of main body 108. First bone plate 300 can include a top surface 302 and an opposing bone contact surface 304 that are substantially planar. One or more through holes 306 can be formed within first bone plate 300 to receive bone screws that are then threaded into the bone to secure first bone mount 110 to the bone, as is known by one skilled in the art. First bone plate 300, as well as the other bone plates discussed herein, can be made of a biocompatible metal (such as, e.g., titanium), alloy, ceramic, polymer or other biocompatible material known by one skilled in the art. If desired, bone contact surface 304 can be sand blasted or otherwise abraded to provide a rough surface for contact with the bone.

As shown in FIG. 2A, first bone plate 300 can include a pair of substantially linear sections 232a and 232b extending in opposite orthogonal directions away from main body to second ends 234a and 234b. Secondary sections 236a and 236b can extend at substantially right angles from each corresponding second end 234a and 234b so as to be substantially parallel to main body 108. Each of sections 232 and 236 can include through holes 306 formed therein. In some embodiments, secondary sections 236 can be excluded so that first bone plate 300 is substantially linear. Other configurations can also be used as is known by one skilled in the art. Generally any symmetrical or assymetrical shape can be used for first bone plate depending on the shape of the lateral mandibular surface and the place of inferoalveolar nerve of the mandible. First bone plate 300 can be secured to outer surface 214 of main body 108 by casting, welding, adhesives, threaded engagement, or other method known by one skilled in the art. Alternatively, first bone mount 110 can be integrally formed with main body 108.

Figure 4:
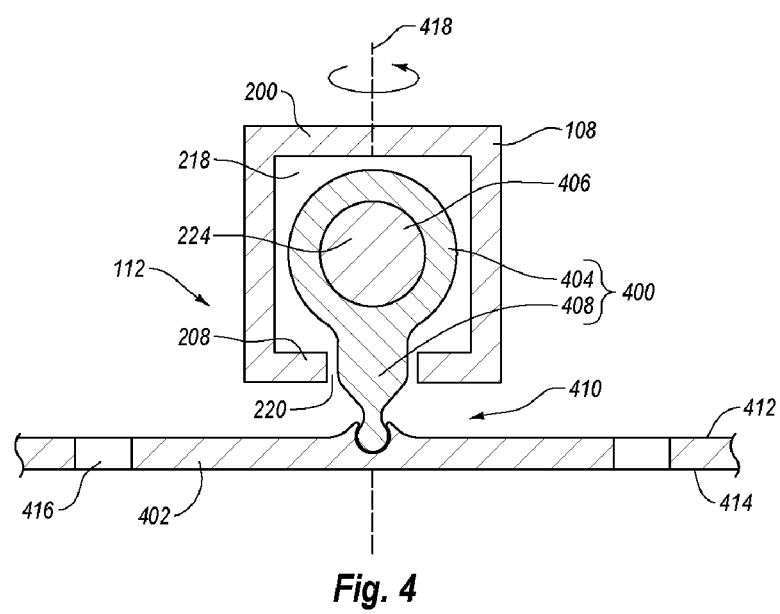
FIG. 4 is a cross sectional view of the mandibular distractor depicted in FIG. 2A taken along the section line 4-4 to show details of a second bone mount.

FIG. 4 is a cross sectional view of distractor 100 taken along the section line 4-4 of FIG. 2A to show details of second bone mount 112. Similar to FIG. 2B, FIG. 4 depicts top wall 200 of main body 108, which is removed from FIG. 2A. Turning to FIG. 4 in conjunction with FIG. 2A, second bone mount 112 can include an engaging member 400 and a second bone plate 402 attached thereto. Engaging member 400 can include an annular engaging body 404 having a threaded bore 406 that is configured to mate with the threads of screw drive 224. Engaging body 404 can be positioned within bore 218 of main body 108 so that screw drive 224 is received within bore 406 of engaging body 404. As such, as screw drive 224 is rotated about central longitudinal axis 202, engaging body 404 can move longitudinally along screw drive 224 due to the mating threads. If another type of drive mechanism is used, second bone mount 112 can be moved longitudinally along main body 108 in a similar manner using a type of engaging member corresponding to the type of drive mechanism. Furthermore, because of the coupling of engaging body 404 to screw drive 224, second bone mount 112 is also prevented from moving longitudinally unless screw drive 224 is rotated. This allows for the widening of the gap between the bone portions only when desired.

Engaging member 400 can also include a connecting member 408 extending radially away from engaging body 404. Connecting member 408 can extend through channel 220 of main body 108 to a distal end 410 that is coupled with second bone plate 402. Connecting member 408 can be attached to engaging body 404 or integrally formed therewith, as is known by one skilled in the art.

Similar to first bone plate 300, second bone plate 402 can include a top surface 412 and an opposing bone contact surface 414 that are substantially planar. One or more through holes 416 can be formed within second bone plate 402 to receive bone screws used to secure second bone plate 402 to the bone. Bone contact surface 414 of second plate 402 can be coplanar with bone contact surface 304 of first bone plate 300, although this is not required. In some embodiments second bone plate 402 can be integrally formed with connecting member 408.

In other embodiments, means for coupling second bone plate 402 to connecting member 408 can be included. For example, if desired second bone plate 402 can be rigidly secured to connecting member 408. In those embodiments, the means for coupling can include welding, adhesives, threaded engagement, or other means known by one skilled in the art. Alternatively, the means for coupling can be configured to allow second bone plate 402 to rotate with respect to engaging member 400. In one embodiment, the means for coupling can include a hinge-like connection that allows second bone plate 402 to rotate about a rotational axis 418 that is substantially perpendicular to bone contact surface 414 of second bone plate 402. That is, the hinge-like connection can allow second bone plate 402 to rotate with respect to engaging member 400 in a single plane, similar to a door hinge.

Figure 5:
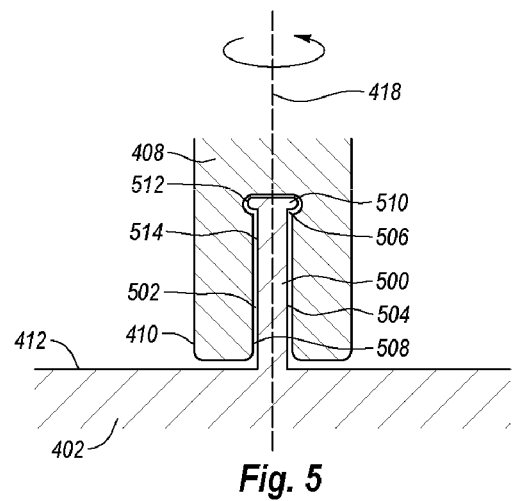
FIG. 5 is a cross sectional view of an illustrative embodiment of a means for coupling the second bone plate to the connecting member.

For example, as shown in FIG. 5, the means for coupling can include a pin 500 and a corresponding receiving bore 502 that receives pin 500 in a hinge-like manner. Pin 500 can include an outer surface 504 extending up from top surface 412 of second bone plate 402 to a distal end 506 along rotational axis 418. Receiving bore 502 can be bounded by an inner surface 508 extending into connecting member 408 from distal end 410 and can be sized to receive pin 500. As such, when pin 500 is received within receiving bore 502, pin 500 can rotate with respect to receiving bore 502 in a single plane about rotational axis 418, thereby moving as a hinge. As a result, second bone plate 402 can be rotatable with respect to main body 108 about rotational axis 418, which can be substantially perpendicular to the plane formed by bone contact surface 414 (not shown) of second bone plate 402. This rotation is represented by the dashed lines 402' in FIG. 2A.

In some embodiments, second bone plate 402 can rotate up to 15 degrees, up to 30 degrees, or up to 45 degrees in either direction from its original position. Other rotational amounts are also possible. It is appreciated that instead of pin 500 being formed on second bone plate 402 and receiving bore 502 being formed on connecting member 408, pin 500 and receiving bore 502 can instead be formed on the opposite surfaces. That is, pin 500 can be formed on connecting member 408 and receiving bore 502 can be formed on second bone plate 402, if desired.

To secure pin 500 within receiving bore 502 while allowing pin 500 to pivot therein, a securing member and corresponding receiver can be positioned anywhere on pin 500 and receiving bore 502. For example, as shown in FIG. 5, pin 500 can include a securing member 510 at distal end 506 that is sized to fit within a receiver 512, which can be a larger portion of a distal end 514 of receiving bore 502. Other types and positions of securing members and receivers can alternatively be used. For example, instead of being positioned at distal end 514, one or more securing members and corresponding receivers can be formed respectively on outer surface 504 of pin 500 and inner surface 508 of receiving bore 502.

In another embodiment, the means for coupling can be configured to allow pivoting of second bone plate 402 with respect to connecting member 408 in conjunction with the rotation about rotational axis 418. For example, the means for coupling can include a coupling receiver formed on top surface 412 of second bone plate 402 and a mating pivoting coupling member formed or attached to distal end 410 of connecting member 408.

Figure 6:
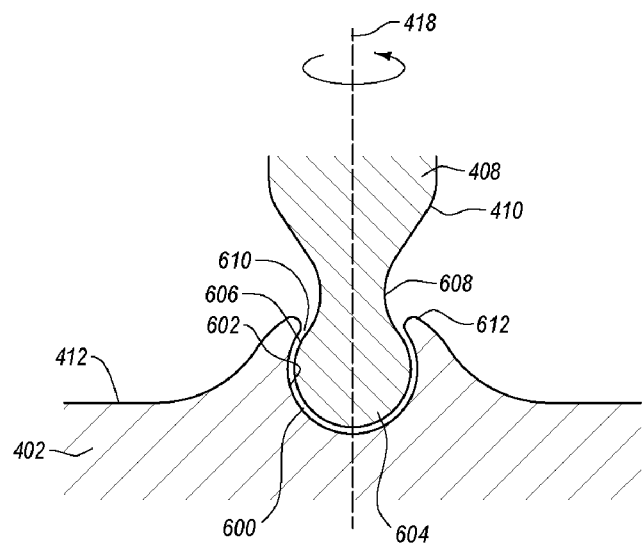
FIG. 6 is a cross sectional view of another illustrative embodiment of a means for coupling the second bone plate to the connecting member.

For example, as shown in FIG. 6, a coupling receiver 600 in the form of a cup or socket having an inner surface 602 can be formed on top surface 412 of second bone plate 402. A coupling member 604 in the form of a ball having an outer surface 606 can be formed on distal end 410 of connecting member 408. Coupling member 604 can be attached to or otherwise extend from connecting member 408 through a neck 608 that has a smaller cross-sectional diameter than coupling member 604.

Coupling receiver 600 can be formed so as to bound an aperture 610 having a constricting rim 612 at the opening thereof. Coupling member 602 can be inserted into coupling receiver 600 so that outer surface 606 of coupling member 604 is positioned against inner surface 602 of coupling receiver 600. When positioned thusly, neck 608 is positioned adjacent constricting rim 612, as depicted in FIG. 6. In this position, coupling member 602 can rotate and pivot within coupling receiver 600 while constricting rim 612 prevents coupling member 602 from exiting coupling receiver 600. Because of the spherical shape of coupling receiver 600 and coupling member 602, coupling member 602 is able to pivot in any direction as coupling member 602 rotates about rotational axis 418. As a result, second bone plate 402 is rotatable with respect to main body 108 in many directions.

Besides constricting rim 612, other means of securing coupling member 602 within coupling receiver 600 can alternatively be used. For example, a set screw or other projecting member can be inserted into or through coupling receiver 600 instead of or in conjunction with constricting rim 612. Furthermore, it is appreciated that if desired, coupling receiver 600 can alternatively be formed on connecting member 408 and coupling member 602 can alternatively be formed on second bone plate 402.

Figure 7:
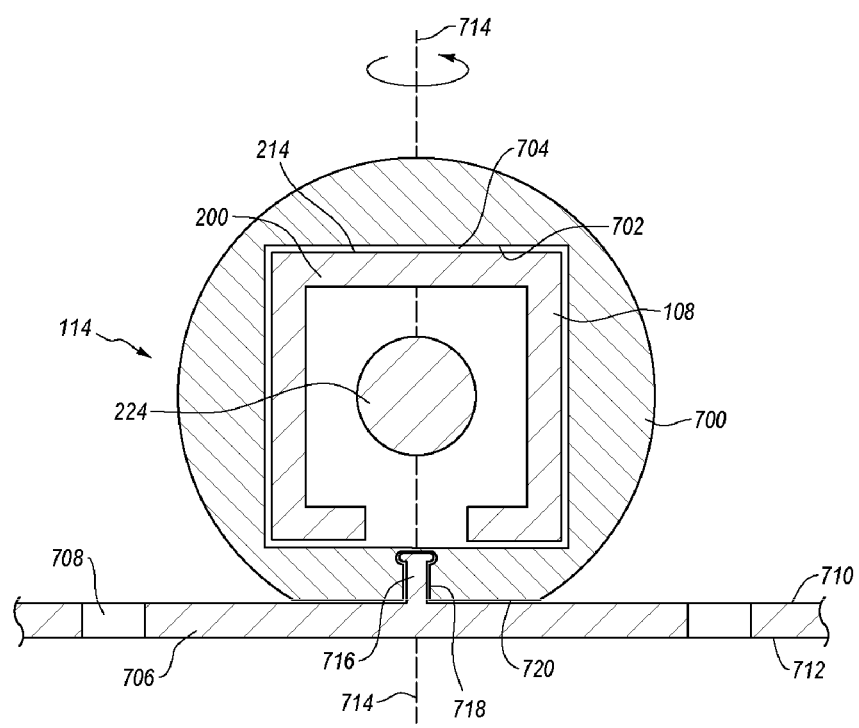
FIG. 7 is a cross sectional view of the mandibular distractor depicted in FIG. 2A taken along the section line 7-7 to show details of a third bone mount.

FIG. 7 is a cross sectional view of distractor 100 taken along the section line 7-7 of FIG. 2A to show details of third bone mount 114. Similar to FIG. 2B, FIG. 7 depicts top wall 200 of main body 108, which is removed from FIG. 2A. Similar to second bone mount 112, third bone mount 114 can be configured to move longitudinally along main body 108. However, unlike second bone mount 112, third bone mount 114 does not necessarily couple with a drive mechanism. In some embodiments, third bone mount can freely move along main body 108, and along curved guide rail 116 when used, without being coupled with a drive mechanism.

Turning to FIG. 7 in conjunction with FIG. 2A, third bone mount 114 can include a sliding member 700 having an inner surface 702 bounding an aperture 704 that extends longitudinally completely through sliding member 700. Sliding member 700 can be slidably positioned on main body 108 so that inner surface 702 of sliding member 700 longitudinally slides on outer surface 214 of main body 108. Sliding member 700 can be in the form of a ring or other desired shape. Sliding member 700 can be generally spherical (i.e., have a rounded outer section) as depicted, to make sliding easier in the body, although this is not required. Sliding member 700 can alternatively have a squared off outer section and/or can be of various thicknesses, if desire, other shapes are also possible. Furthermore, sliding member 700 can radially encircle the entire main body 108 or any portion thereof.

Third bone mount 114 can include a third bone plate 706 attached to sliding member 700. Similar to first and second bone plates 300 and 402, third bone plate 706 can include a top surface 710 and an opposing bone contact surface 712 that are optionally substantially planar. One or more through holes 708 can be formed within third bone plate 706 to receive bone screws used to secure third bone plate 706 to the bone. Bone contact surface 712 of third bone plate 706 can be coplanar with bone contact surface 304 of first bone plate 300 and/or bone contact surface 414 of second bone plate 402, although this is not required. Third bone plate 706 can be rigidly secured to sliding member 700 or integrally formed therewith, in a similar manner to that described previously with regard to second bone plate 402 and connecting member 408.

Alternatively, means for coupling third bone plate 706 to sliding member 700 can be included. The means for coupling can be configured to allow third bone plate 706 to rotate with respect to sliding member 700. In one embodiment, the means for coupling can include a hinge-like connection similar to the hinge like connection discussed above with regard to second bone mount 112. That is, the means for coupling third bone plate 706 to sliding member 700 can include a hinge like connection that allows third bone plate 706 to rotate about a rotational axis 714 that is substantially parallel to bone contact surface 712. For example, as shown in FIG. 7, the means for coupling can include a pin 716 projecting from top surface 710 of third bone plate 706 and a corresponding receiving bore 718 formed on a bottom surface 720 of sliding member 700.

Alternatively, pin 716 and receiving bore 718 can be formed respectively on bottom surface 720 and top surface 710, if desired. Pin 700 and bore 718 can have the same structure and properties as pin 500 and receiving bore 502 discussed previously. A securing member and corresponding receiver similar to those described above with respect to second bone mount 112 can also be positioned anywhere on pin 716 and receiving bore 718 to secure pin 716 within receiving bore 720 while still allowing pin 716 to rotate therein.

Using pin 716 and receiving bore 718, third bone plate 706 can be rotatable with respect to main body 108 about rotational axis 714 that is substantially perpendicular to the plane formed by bone contact surface 712 of third bone plate 706. This rotation is represented by the dashed lines 706' in FIG. 2A. In some embodiments, third bone plate 706 can rotate up to 15 degrees, up to 30 degrees, or up to 45 degrees in either direction from its original position. Other rotational amounts are also possible.

Also similar to the means for coupling associated with the second bone mount, the means for coupling third bone plate 706 to sliding member 700 can be configured to allow pivoting of third bone plate 706 with respect to sliding member 700 in conjunction with the rotation about rotational axis 714. For example, a coupling member and coupling receiver similar to those discussed above with regard to second bone mount 112 can be used with third bone mount 114. The coupling member can be formed on sliding member 700 or third bone plate 706 and the corresponding coupling receiver can be formed on the opposite structure. As such, when assembled, the coupling member can rotate and pivot within the coupling receiver, similar to that described above. As a result, using a coupling member and a coupling receiver will allow third bone plate 706 to be rotatable with respect to main body 108 in many directions.

Returning to FIG. 2A, guide rail 116 can include a top wall 250, a bottom wall 252 (see FIG. 8), and opposing side walls 254, 256 extending from a first end 258 to a second end 260 along a curved path. In the depicted embodiment, guide rail 116 defines a substantially arcuate path. In other embodiments guide rail can define a substantially parabolic, hyperbolic, or other regular or non-regular path. Other paths can also be used. Walls 250, 252, 254, and 256 can collectively have an outer surface 262 facing away from guide rail 116.

First end 258 of guide rail 116 can be attached to second end 206 of main body 108 so that the curved path defined by guide rail 116 begins and extends from second end 206 of main body 108. Guide rail 116 can have a cross sectional outer shape that is substantially the same as the cross sectional outer shape of main body 108. For example, guide rail 116 can have a substantially square cross sectional outer shape sized to match the shape of main body 108. Other shapes are also possible to match the cross sectional shape of main body 108. Because of the matching cross sectional shapes, when third bone mount 114 reaches the second end 206 of main body 108, third bone mount 114 can continue smoothly sliding along outer surface 262 of guide rail 116.

Figure 8:
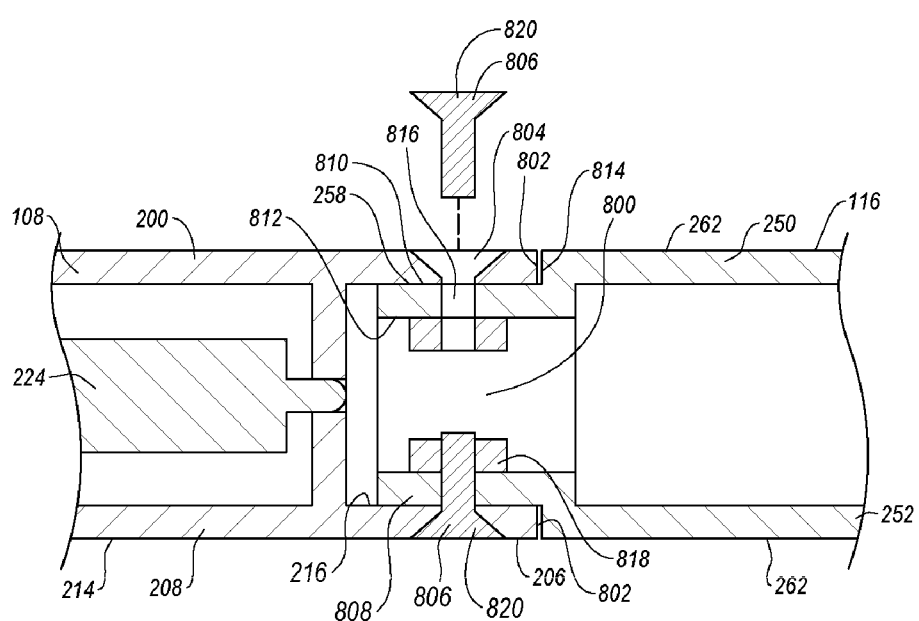
FIG. 8 is a cross sectional partial view of a mandibular distractor showing an illustrative manner of attaching the guide rail to the main body.

Guide rail 116 can be attached to main body 108 in a manner that does not constrict the movement of third bone mount 114 as third bone mount moves between main body 108 and guide rail 116. FIG. 8 is a close up view of one illustrative manner of attaching guide rail 116 to main body 108. As shown in FIG. 8, main body 108 can be open at second end 206 such that inner surface 216 can bound a bore 800 that extends longitudinally into main body 108 from a second end face 802. One or more through holes 804 can be formed on one or more of the top and bottom walls 200, 208 and/or one or more of the side walls 210, 212 (FIG. 2A) for inserting screws 806 therethrough. To prevent inner surface 702 of third bone mount 114 from catching on screws 806, through holes 804 can be countersunk, as shown.

A constricted portion 808 of guide rail 116 can be formed by top and bottom walls 250, 252 and/or one or more of side walls 254, 256 (FIG. 2A) at first end 258. At constricted portion 808, each of walls 250, 252, 254, and 256 (FIG. 2A) can be positioned radially inward (i.e., towards each other), so that constricted portion 808 can have an outer surface 810 and an opposing inner surface 812. Due to the constriction, outer surface 810 can be separated from outer surface 262 by a ledge 814. Outer surface 810 can have a cross sectional shape and size generally matching those of inner surface 216 of main body 108 at second end 206 thereof. As a result, constricted portion 808 can be inserted into bore 800 so that outer surface 810 thereof can be adjacent to inner surface 216 and ledge 814 can abut second end face 802, as depicted in FIG. 8. One or more through holes 816 can be formed on one or more of walls 250, 252, 254, and 256 (FIG. 2A) to align with through holes 804 on main body 108 when constricted portion is positioned within bore 800.

Once constricted portion 808 has been received within bore 800, screws 806 can be inserted into through holes 804 and 816 and threaded into nuts 818 that have been secured to inner surface 812. Alternatively, nuts 818 can be omitted and screws 806 can be threaded directly into through holes 816 if desired. As a result of the countersunk through holes 804, heads 820 of screws 806 do not project past outer surface 214 of main body 108 and therefore do not impede movement of third bone mount 114 as third bone mount moves from main body 108 to guide rail 116.

It is appreciated that instead of first end 258 of guide rail 108 being received within second end 206 of main body 108, second end 206 of main body 108 can be received within first end 258 of guide rail 108. That is, bore 800 and constricted portion 808 can be formed on the opposite surfaces so that a constricted portion of second end 206 of main body 108 can be received within a bore formed on first end 258 of guide rail 108. In those embodiments, through holes 816 can be countersunk on guide rail 116 and nuts 818 can be secured to inner surface 216 of main body 108.

Figure 9:
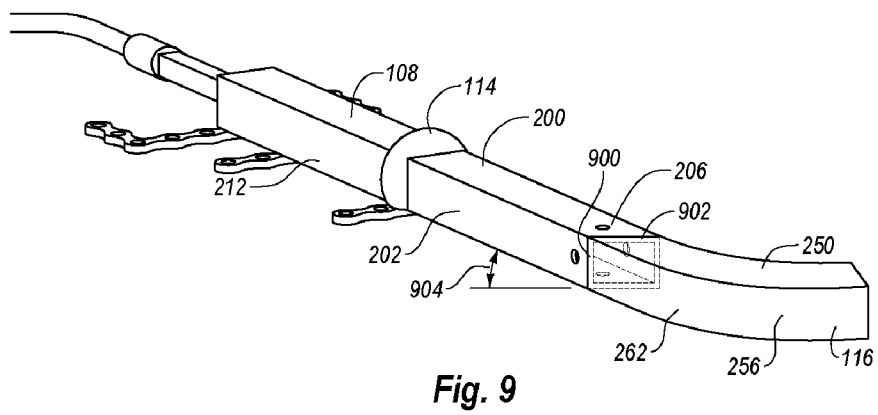
FIG. 9 is a perspective view of an illustrative embodiment of a mandibular distractor.

Second end face 802 and ledge 814 come together to form traversing interfaces between the outer surfaces 214 and 262 of main body 108 and guide rail 116. For example, as shown in FIG. 9, traversing interface 900 is formed where side wall 212 of main body 108 and side wall 256 of guide rail 116 come together. Similarly, traversing interface 902 is formed where top wall 200 of main body 108 and top wall 250 of guide rail 116 come together. The traversing interfaces can be substantially orthogonal with respect to a plane defined by the longitudinal axis 202 or can form an acute angle thereto.

For example, in the embodiment depicted in FIG. 9, traversing interface 900 traverses side walls 212 and 256 in a substantially orthogonal manner, and traversing interface 902 traverses top walls 200 and 250 in a substantially non-orthogonal manner, forming an acute angle 904 between interface 902 and main body 108. Acute angle 904 can be between 45 and 90 degrees in some embodiments. In other embodiments, acute angle 904 can be between 60 and 90 degrees. Other angles can alternatively be used. Forming a non-orthogonal interface angle may be beneficial to prevent third bone mount 114 from catching on the interface as bone mount 114 moves from main body 108 to guide rail 116.

Other manners of attaching guide rail 116 to main body 108 can alternatively be used. For example, adhesives, other types of fasteners, or press fitting can be used to secure guide rail 116 to main body 108. Alternatively, guide rail 116 can be integrally formed with main body. Other manners of attachment are also possible.

Figure 10:
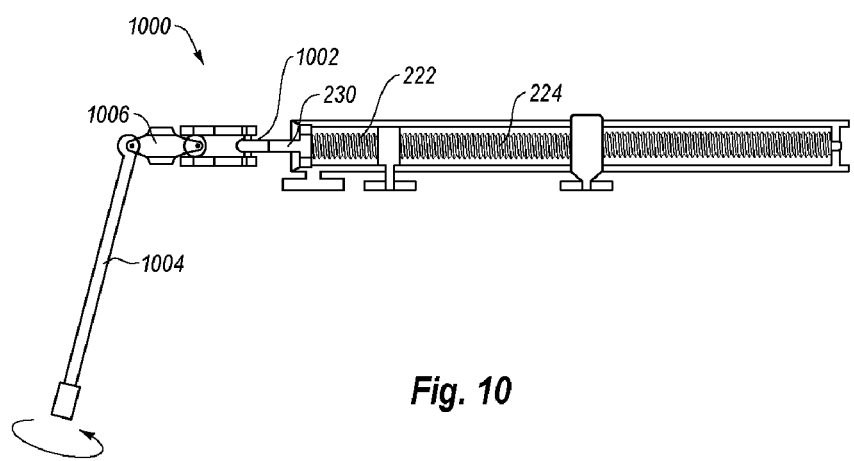
FIG. 10 is a side view of an illustrative embodiment of a mandibular distractor with a side wall of the main body removed to show details within the main body.

FIG. 10 is a side view of an illustrative embodiment of a distractor with the closest side wall of main body 108 removed for clarity. Turning to FIG. 10, a drive actuator 1000 can be used to selectively engage and activate the drive mechanism 222. As such, drive actuator 1000 can include a second coupler 1002 configured to couple with first coupler 230 on drive mechanism 222. Second coupler 1002 can be of a form which mates with first coupler 230. For example, second coupler 1102 can be a key, a socket, or a latching mechanism that mates with first coupler 230. Other types of coupling elements as are known by those skilled in the art can also be used. Furthermore, if desired, drive actuator 1000 can be removable from drive mechanism 222. For those embodiments, second coupler 1002 is removable from first coupler 230. Drive actuator 1000 can also include a handle 1004 or other means to allow a user or machine to manipulate drive actuator 1000. Handle 1004 can extend away from main body 108 so as to allow easier access thereto. A universal joint 1006 can be positioned between handle 1004 and second coupler 1002 to aid in manipulating drive actuator 1000, if desired. The universal joint 1006 can allow handle 1004 to be positioned in various orientations with regard to drive mechanism 222 while allowing handle 1004 to actuate the drive mechanism. Handle 1004 and universal joint 1006 are sized to be able to fit within the mouth or other body portion comfortably while being used to manipulate drive mechanism 222.

Once second coupler 1002 is connected to first coupler 230, drive mechanism 222 can be actuated. For example, in the depicted embodiment, rotating handle 1004 of drive actuator 1000 causes second coupler 1002 to rotate, which causes first coupler 230 and screw drive 224 to rotate. As discussed above, drive actuator 1000 can be configured to be detachable from drive mechanism 222 if desired so that drive actuator 1000 can be removed once drive mechanism 222 has been rotated a desired amount. Other types of drive actuators can alternatively be used as is known by one skilled in the art.

Using embodiments of the distractor 100, two portions of a bone can be caused to move both linearly as well as arcuately with respect to each other during distraction osteogenesis. For example, a method of performing distraction osteogenesis can include attaching a first bone mount to a first bone portion, the first bone mount being secured to an elongated main body of a mandibular distractor, the main body having a central longitudinal axis extending in the elongate direction between a first end and a spaced apart second end. The method can further include attaching a second bone mount to a second bone portion, the second bone mount being positioned on the main body. The method can further include attaching a third bone mount to the second bone portion, the third bone mount being associated with the main body. The method can further include activating a drive mechanism to selectively move the second bone mount longitudinally along the main body away from the first bone mount, thereby causing the second bone portion to separate from the first bone portion. The method can further include activating the drive mechanism to selectively move the second bone mount further longitudinally along the main body, thereby causing the second bone portion to arcuately separate from the first bone portion.

The act of activating the drive mechanism can include rotating a screw drive positioned within a bore of the main body, the screw drive being engaged with the second bone mount. The act of activating the drive mechanism can cause the second bone portion to linearly or arcuately separate from the first bone portion. The act of activating the drive mechanism can cause a bone plate of the second bone mount or the third bone mount to rotate with respect to the main body about an axis that is substantially perpendicular to the central longitudinal axis of the main body. The bone plates of the second or third bone mounts can rotate with respect to the main body about axes that can be substantially perpendicular to the central longitudinal axis of the main body. Movement of the second bone mount can cause the third bone mount associated with the main body to move along a curved guide rail attached to the main body. The first and second bone portions can be separate first and second portions of a mandible.

Figure 11A:
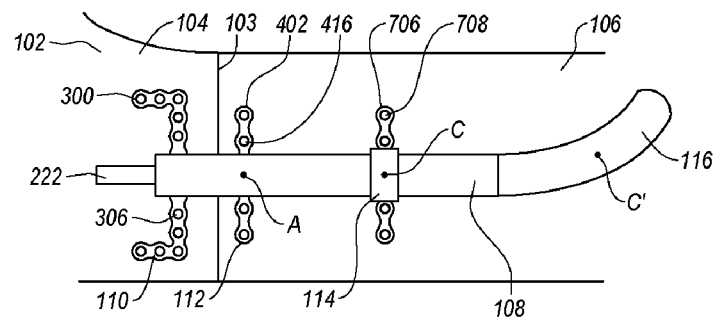
FIGS. 11A-11C are top views of an illustrative embodiment of a method of performing distraction osteogenesis with the system described herein.
Figure 11B:
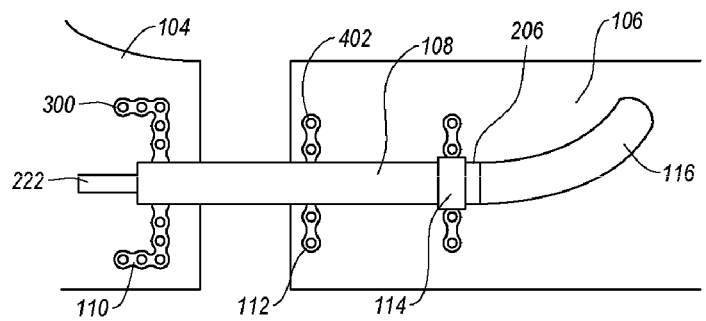
Figure 11C:
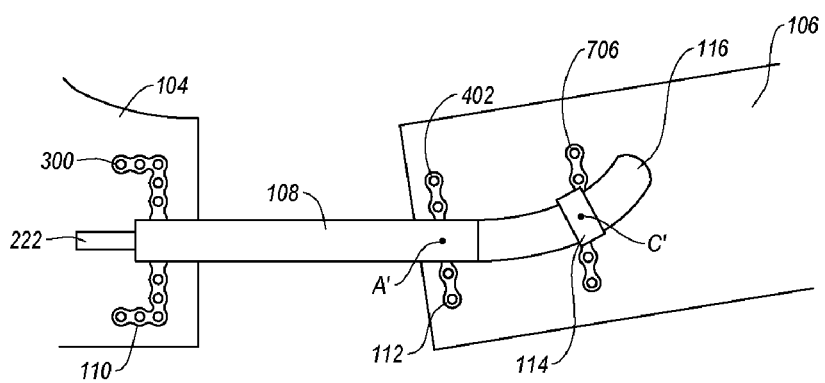

Referring to FIGS. 11A-11C, an illustrative method of performing distraction osteogenesis will now be discussed using the embodiment of the mandibular distractor discussed above.

Lower jaw 102 is first separated into first bone portion 104 and second bone portion 106 along separation line 103, as is known in the art. Then, first bone mount 110 is attached to first bone portion 104 and second and third bone mounts 112 and 114 are attached to second bone portion 106 while first and second bone portions 104 and 106 remain abutting each other, as shown in FIG. 11A. This can be done by attaching bone plates 300, 402, and 706 directly to the bone. The attachment of bone plates 300, 402, and 706 to bone can be performed by passing bone screws through through holes 306, 416, and 708 within the bone plates and threading the bone screws into the bone, although other attachment methods can alternatively be used, as is known in the art. Bone plates 300, 402, and 706 can be attached in any order desired, although a typical order would be to attach first, second, and third bone plates 300, 402, and 706 in that order. As can be seen in FIG. 11A, second and third bone plates 402, and 706 can extend laterally away from main body in a substantially orthogonal manner, although this is not required. Second and third bone mounts 112 and 114 can each include means for coupling, as described above, that allow second and third bone plates 402 and 706 to rotate with respect to main body 108.

As identified in FIG. 11A, second and third bone mounts 112 and 114 are initially positioned on main body 108 at points A and C, respectively. Further discussion is set forth below regarding one manner of determining the location of points A and C on main body 108, as well as determining the location on guide rail 116 where the third bone mount will lie (denoted C' on FIG. 11A) when second bone portion 106 is positioned in the final, distracted location.

Once bone mounts 110, 112, and 114 are attached to first and second bone portions 104 and 106, drive mechanism 222 is activated to selectively move second bone mount 112 longitudinally along main body 108 away from first bone mount 110. This causes second bone portion 106 to separate from first bone portion 104, as shown in FIG. 11B. As noted above, drive mechanism 222 can include rotating screw drive 224 (see FIG. 2A) that is activated by using drive actuator 1000 (see FIG. 10).

As shown in the depicted embodiment, because third bone mount 114 is also attached to second bone portion 106, third bone mount 114 moves the same distance longitudinally along main body 108 as does second bone mount 112. In the depicted embodiment, second bone portion 106 separates linearly from first bone portion 104. As such, second and third bone plates 300 and 402 remain extending laterally away from main body 108 in the same substantially orthogonal manner as when first attached to the bone portions.

Drive mechanism 1000 can be further activated to selectively move second bone mount 112 longitudinally further along main body 108 away from first bone mount 110, thus further separating second bone portion 106 from first bone portion 104. Again, because third bone mount 114 is attached to second bone portion 106, third bone mount also continues to be moved longitudinally along main body 108.

At some point, however, third bone mount 114 may reach second end 206 of main body 108 and begin to move along curved guide rail 116. At this point, further activation of drive mechanism 222 causes second bone mount 112 to continue moving longitudinally along main body 108, which in turn causes third bone mount 114 to travel arcuately along guide rail 116. As a result, because first bone mount 110 is rigidly attached to first bone portion 104 and second and third bone mounts 112 and 114 are rotationally attached to second bone portion 106, second bone portion 106 begins to rotate about second bone mount 112 as third bone mount 114 travels arcuately along guide rail 116, as shown in FIG. 11C. Because second and third bone plates 402 and 706 are rigidly attached to second bone portion 106, second and third bone plates 402 and 706 each may rotate with respect to main body 108 as second bone portion 106 rotates.

For example, in the position shown in FIG. 11C, second and third bone plates 402 and 706 are no longer orthogonal to main body 108 as they were to begin with. Instead, second and third bone plates 402 and 706 now form an acute angle with main body 108. This angle can continue to change as third bone plate 706 moves further along curved guide rail 116, causing second bone portion 106 to separate arcuately from first bone portion 104.

The distraction continues until second bone portion 106 is positioned in the desired final position with respect to first bone portion 104. At this final position, second and third bone mounts 112 and 114 will respectively be positioned at points A' and C' on the distractor, as discussed in more detail below. As is known in the art, once the bone portions 104 and 106 have been positioned in the desired locations and enough bone has grown therebetween, the distractor can be removed.

In an alternative embodiment, bite plates as are known in the art can be used instead of third bone mount 114 to impart the arcuate movement to second bone portion 106. For example, bite plates of diminishing thicknesses can be successively positioned between the teeth as drive mechanism 222 is used. The changing thicknesses of the bite plates can cause second bone portion 106 to move closer to the upper jaw as second bone portion 106 is moved further away from first bone portion 104. This in effect causes second bone portion 106 to also move arcuately with respect to first bone portion 104. Because second bone mount 112 can be rotationally attached to second bone portion 106, second bone mount 112 can rotate with respect to second bone portion 106 as second bone portion 106 arcuately moves closer to the upper jaw, similar to embodiments described above. If desired, third bone mount 114 can also be used when using a bite plate.

Figure 12A:
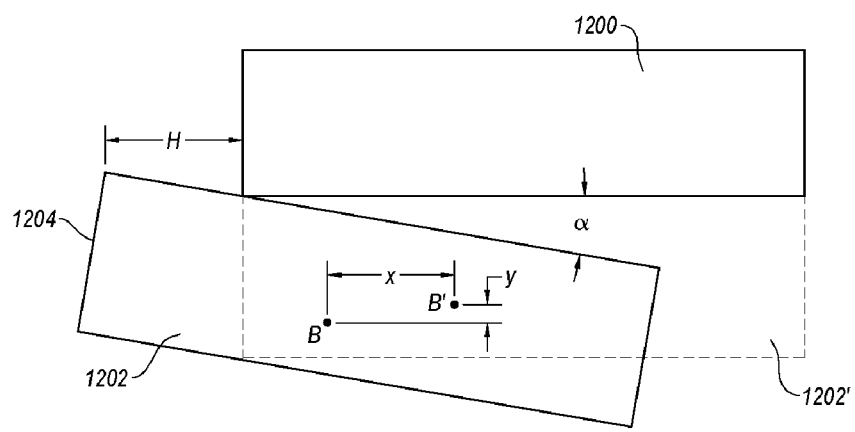
FIGS. 12A-12C show an illustrative embodiment of a method of determining the configuration of a mandibular distractor.
Figure 12B:
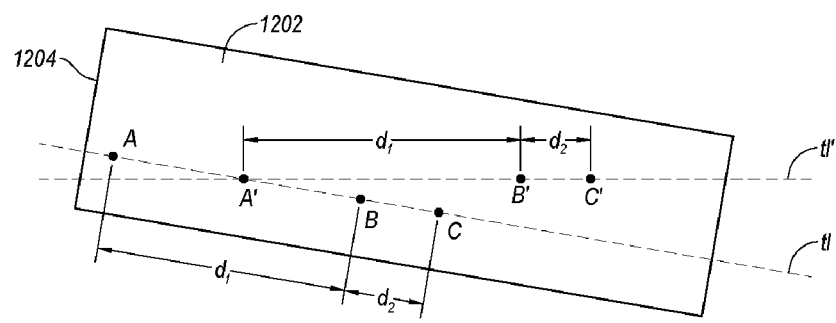
Figure 12C:
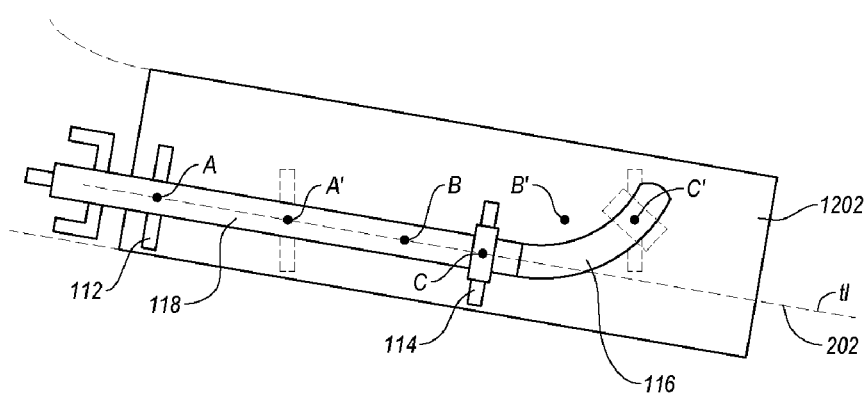

Referring to FIGS. 12A-12C, one method of determining the configuration of a distractor will now be discussed using the embodiment of the mandibular distractor discussed above.

FIG. 12A is a block diagram showing the relationship between an upper portion or maxilla 1200 of a jaw and a corresponding lower portion or mandible 1202 that is in need of distraction. In the example shown, mandible 1202 is horizontally misaligned with maxilla 1200 by a distance denoted as H in the Figure. Mandible 1202 is also rotationally misaligned with maxilla 1200 by an angle $\alpha$. These values of distance H and angle $\alpha$ can be determined, e.g., by a cephalometric method, as is known by one skilled in the art. Using mandibular distraction, mandible 1202 can be moved with respect to maxilla 1200 from the initial position (shown in solid lines and denoted 1202) to a final position (shown in dashed lines and denoted 1202') which is aligned with maxilla 1200. The distraction will occur at the proximal end 1204 of mandible 1202, which has been severed from the rest of the lower jaw, as discussed above.

Once distance H and angle $\alpha$ are determined, the amount and direction of movement of any point of mandible 1202 required to fully distract mandible 1202 can then be calculated. To do so, any point can be selected on pre-distracted mandible 1202 and a unique corresponding point corresponding to the post-distracted mandible 1202' can then be determined. For example, in FIG. 12A, a point B on pre-distracted mandible 1202 will move to point B' when mandible 1202 is fully distracted (i.e., in position 1202'). Point B' can be determined by simple graphing or calculation means. For example, point B will move a horizontal distance x and a vertical distance y to arrive at point B'. Some of this movement will be rotational to overcome the rotational misalignment $\alpha$. Point B is only an illustrative point; any other point on mandible 1202 can also be chosen to determine the movement that will occur relative to that point. In sum, any point B identified on pre-distracted mandible 1202 will move to a corresponding unique point B' when mandible 1202 is fully distracted. That is, when a preselected point B moves to point B', mandible 1202 has been fully distracted to the desired position.

With the foregoing in mind, the initial positions of the second and third bone mounts can be determined as well as the configuration of the distractor corresponding to any point B and corresponding point B'. For example, with reference to FIG. 12B, once a point B has been chosen and a corresponding point B' determined, a longitudinal traversing line tl can be determined that is parallel to mandible 1202 and passes through point B. Similarly, a longitudinal traversing line tl' can be determined that is parallel to post-distraction mandible 1202' (see FIG. 12A) and passes through point B'. Longitudinal traversing line tl' is likely to be horizontal, although this is not required. Longitudinal traversing lines tl and tl' should intersect with each other at a single point, denoted A' on FIG. 12B. The distance $d_1$ between intersecting point A' and point B' is then determined by measurement or simple calculation. If longitudinal traversing lines tl and tl' do not intersect at a single point (i.e., the lines are collinear or are parallel to each other), then a different point B can be chosen and the process started over.

A unique point on longitudinal traversing line tl is then determined that is the same distance $d_1$ from point B as point A' is from point B'. This unique point is designated as point A on FIG. 12B. Point A should be closer to proximal edge 1204 than point B. As noted above, point A corresponds to the position on mandible 1202 where the second bone mount will be positioned before distraction begins and point A' corresponds to the location on mandible 1202 where the second bone mount will have moved to once distraction has been completed.

A point is then chosen on longitudinal traversing line tl' that lies on the opposite side of point B' as point A'. This point is designated point C' on FIG. 12B. The exact position of point C' along longitudinal traversing line tl' can vary, although point C' should be chosen so that it lies within the borders of pre-distracted mandible 1202. The distance $d_2$ between point B' and point C' is then determined by measurement or calculation.

A unique point on longitudinal traversing line tl is then determined that is the same distance $d_2$ from point B as point C' is from point B'. This unique point is designated as point C on FIG. 12B. Point C should lie on the opposite side of point B as point A. As noted above, the exact position of point C' along longitudinal traversing line tl' can vary. However, point C should be the same distance $d_2$ from point B as point C' is from point B'. As noted above, point C corresponds to the position on mandible 1202 where the third bone mount will be positioned before distraction begins and point C' corresponds to the location on mandible 1202 where the third bone mount will have moved to once distraction has been completed.

Using the above manner of determining where longitudinal traversing line tl and points A, A', C, and C' lie on mandible 1202, the configuration of distractor 100 as well as the starting positions for the second and third bone mounts thereof can be determined. With reference to FIG. 12C, main body 108 is positioned on mandible 1202 so that longitudinal axis 202 aligns with longitudinal traversing line tl and passes through points A and C. As noted above, second and third bone mounts 112 and 114 are initially positioned and subsequently secured to mandible 1202 so as to respectively align with points A and C. Guide rail 116 is designed and positioned such that guide rail 116 passes through point C', which is the where third bone mount 114 will move to once the distraction has been completed. The actual curvature of guide rail 116 can vary, as long as guide rail 116 passes through point C'. As noted above, point A' is where first bone mount 112 will move to once the distraction has been completed, so main body 108 should also align with point A'.

The method of determining the configuration and position of a distractor discussed above is only illustrative and variations in the method or other methods can also be used. For example, many of the steps discussed above can be performed in a different order than presented. As an example of this, point C can be chosen first and then point C' determined, if desired.

Figure 13A:
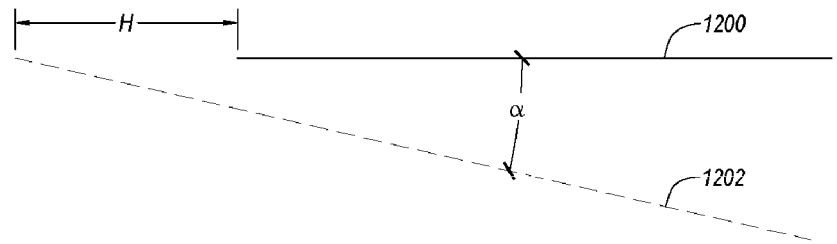
FIGS. 13A-13C show another illustrative embodiment of a method of determining the configuration of a mandibular distractor.
Figure 13B:
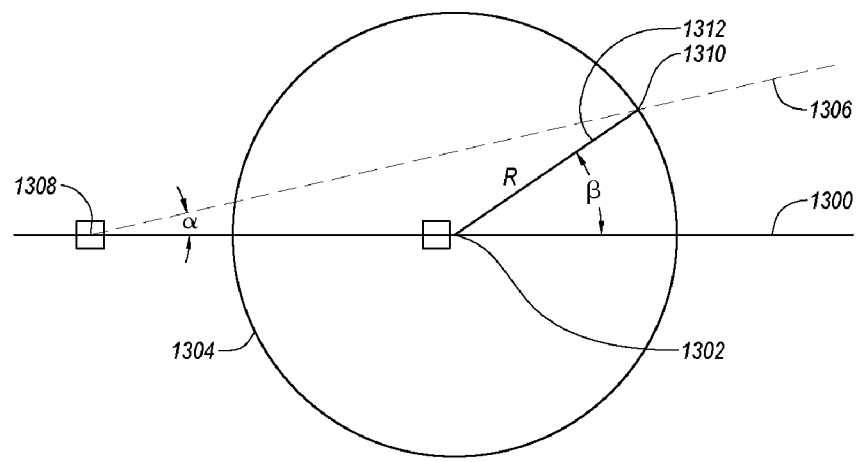
Figure 13C:
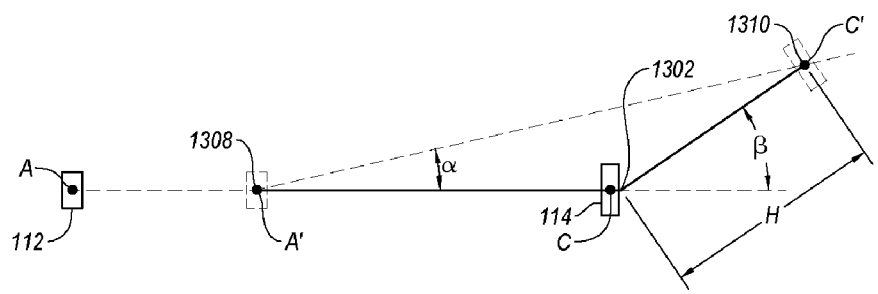

Referring to FIGS. 13A-13C, another illustrative method of determining the configuration of a distractor will now be discussed. This method allows for a simple calculation to be used.

FIG. 13A is a schematic representation of the maxilla 1200 and mandible 1202 shown in FIG. 12A, with H once again representing the horizontal misalignment and angle α representing the rotational misalignment. As shown in FIG. 13B, to determine the dimensions of distractor 100, a straight line 1300 is drawn and a point 1302 on the line is chosen. Line 1300 can be horizontal, although this is not required. A circle 1304 is then drawn having its center at point 1302 and a radius R equal to the horizontal misalignment H. A second straight line 1306 is then drawn so as to pass through both line 1300 and circle 1304, angling away from line 1300 by angle α. The line 1306 should intersect line 1300 at a point 1308 and the far side of the circle at a point 1310. A line 1312 is then drawn from the center point 1302 of circle 1304 to point 1310. Because point 1310 is on the circle, the distance of line 1312 corresponds to the radius R of the circle, which is equal to horizontal misalignment H. An angle β is formed between lines 1312 and 1300.

As shown in FIG. 13C, when the distractor is designed, point 1308 where lines 1300 and 1306 intersect corresponds to where second bone mount 112 can be positioned when distraction has been completed (i.e., analogous to point A' in FIG. 12C) and center point 1302 corresponds to point C where third bone mount 114 can be initially positioned. Point 1310 corresponds to point C' where third bone mount 114 can be positioned when distraction has been completed. Using this information, the initial position point A for second bone mount 112 can be obtained by simply geometrically or empirically determining where second bone mount 112 will be when third bone mount 114 is in its initial position point C.

Other variations and other methods are also possible to determine the configuration and/or position of a distractor.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A mandibular distractor comprising:
an elongated main body defining an internal bore having a central longitudinal axis extending in an elongate direction between a first end having a first opening and a spaced apart second end and the main body having an open slot in communication with the internal bore and extending from the first end to the second end;
a screw drive mechanism having an elongate screw drive bolt located within the internal bore of the main body and a coupler protruding from the first open end;
a first bone mount having a first bone plate fixedly secured to the first end of the main body and being configured to attach to a first bone portion;
a second bone mount including an engaging member that is threadedly coupled with the elongate screw drive bolt in the internal bore and including a second bone plate positioned outside of the main body that is hingedly attached to the engaging member through the open slot, the bone plate being configured to attach to a second bone portion;

a third bone mount having a collar freely slidably mounted to the elongated main body, and having a third bone plate mounted to the collar, and being configured when the second bone mount and third bone mount are attached to the second bone portion to move longitudinally along the main body when the second bone mount is moved by the screw drive mechanism; and a curved guide rail attached to the second end of the main body, wherein the collar of the third bone mount is located between the second bond mount and a free end of the curved guide rail.

2. The mandibular distractor of claim 1, wherein the first bone mount is configured as one or more of the following:
the first bone mount includes the first bone plate coupled to an outside surface of the main body; or
the first bone mount includes the first bone plate rigidly secured to an outside surface of the main body.

3. The mandibular distractor of claim 1, wherein the third bone mount includes
the third bone plate being hingedly attached to the collar.

4. The mandibular distractor of claim 3, wherein the collar is substantially circular.

5. The mandibular distractor of claim 3, wherein the third bone plate is rotatable with respect to the main body about a rotational axis.

6. The mandibular distractor of claim 1, wherein the screw drive mechanism includes the screw drive bolt rotationally coupled with the main body so that the screw drive bolt rotates with respect to the main body.

7. The mandibular distractor of claim 1, wherein the main body has an inner surface bounding the bore extending longitudinally between the first and second ends, and an end of the screw drive bolt is rotationally mounted to the second end.

8. The mandibular distractor of claim 1, further comprising the curved guide rail being received into the second end of the main body.

9. The mandibular distractor of claim 8, wherein the third bone mount is freely slidable along an external surface of the curved guide rail.

10. The mandibular distractor of claim 8, wherein the guide rail is substantially arcuate and has a similar cross sectional shape as the main body.

11. The mandibular distractor of claim 1, wherein the central longitudinal axis is substantially linear.

12. The mandibular distractor of claim 1, further comprising a drive actuator that engages and activates the screw drive mechanism.

13. The mandibular distractor of claim 12, wherein the drive actuator includes a coupler.

14. The mandibular distractor of claim 13, wherein the screw drive mechanism includes the elongate screw drive bolt engaged with the coupler.

15. The mandibular distractor of claim 12, wherein the drive actuator includes a universal joint and/or a handle.

16. The mandibular distractor of claim 1, wherein the second bone plate of the second bone mount is rotatable with respect to the main body.

17. A mandibular distractor system comprising:
the mandibular distractor of claim 1; and
a drive actuator configured to engage and activate the screw drive mechanism.

18. A method of performing distraction osteogenesis, the method comprising:
providing a mandible extractor comprising:
an elongated main body having a central longitudinal axis extending in the elongate direction between a first end and a spaced apart second end;
a first bone mount secured to the main body, the first bone mount being configured to attach to a first bone portion;
a second bone mount positioned on the main body, the second bone mount including:
an engaging member;
a bone plate hingedly attached to the engaging member, the bone plate being configured to attach to a second bone portion; and
a drive mechanism engaged to the engaging member and configured to selectively move the second bone mount longitudinally along the main body;
attaching the first bone mount to the first bone portion, the first bone mount being secured to the elongated main body of the mandibular distractor, the main body having a central longitudinal axis extending in the elongate direction between the first end and the spaced apart second end;
attaching the second bone mount to the second bone portion, the second bone mount being positioned on the main body;
attaching a third bone mount to the second bone portion, the third bone mount being associated with the main body; and
activating a drive mechanism to selectively move the second bone mount longitudinally along the main body away from the first bone mount, thereby causing the second bone portion to separate from the first bone portion,
wherein movement of the second bone mount causes the third bone mount associated with the main body to move along a curved guide rail attached to the main body.

19. The method of claim 18, wherein activating the drive mechanism includes one or more of the following:
causing the second bone portion to arcuately separate from the first bone portion;
causing the second bone portion to linearly separate from the first bone portion;
causing a bone plate of the second bone mount to rotate with respect to the main body about an axis that is substantially perpendicular to the central longitudinal axis of the main body;
causing a bone plate of the third bone mount to rotate with respect to the main body about an axis that is substantially perpendicular to the central longitudinal axis of the main body; or
rotating a screw drive positioned within a bore of the main body, the screw drive being engaged with the second bone mount.

* * * * *

UNITED STATES PATENT AND TRADEMARK OFFICE
CERTIFICATE OF CORRECTION

| | | |
|---|---|---|
| PATENT NO. | : 9,055,976 B2 | Page 1 of 1 |
| APPLICATION NO. | : 13/319148 | |
| DATED | : June 16, 2015 | |
| INVENTOR(S) | : Li | |

It is certified that error appears in the above-identified patent and that said Letters Patent is hereby corrected as shown below:

IN THE SPECIFICATION

In Column 1, Line 6, delete "§371" and insert -- § 371 --, therefor.

In Column 1, Line 22, delete "fraction" and insert -- traction --, therefor.

Signed and Sealed this
Twenty-fourth Day of November, 2015

Michelle K. Lee
*Director of the United States Patent and Trademark Office*